United States Patent
Zhou et al.

(10) Patent No.: US 7,087,433 B2
(45) Date of Patent: Aug. 8, 2006

(54) 7SK RNA REGULATED TRANSCRIPTION

(75) Inventors: Qiang Zhou, Berkeley, CA (US);
Zhiyuan Yang, Berkeley, CA (US);
Qingwei Zhu, Berkeley, CA (US);
Kunxin Luo, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 517 days.

(21) Appl. No.: 10/227,367

(22) Filed: Aug. 25, 2002

(65) Prior Publication Data

US 2004/0038218 A1    Feb. 26, 2004

(51) Int. Cl.
*A61K 48/00* (2006.01)
*C07H 21/04* (2006.01)
*C07H 21/02* (2006.01)
*C12Q 1/68* (2006.01)

(52) U.S. Cl. .................. 436/6; 536/23.1; 536/24.3; 536/24.5; 435/6; 435/325; 435/375; 514/44

(58) Field of Classification Search .................. 435/6, 435/91.1, 91.3, 325, 375; 514/44; 536/23.1, 536/24.3, 24.5
See application file for complete search history.

(56) References Cited

OTHER PUBLICATIONS

Jen et al., Suppression of Gene Expression by Targeted Disruption of Messenger RNA: Available Options and Current Strategies, Stem Cells, 2000, 18:307-319.*
Branch, A good antisense molecule is hard to find, TIBS, Feb. 1998, pp. 45-50.*
Green et al., Antisense Oligonucleotides: An Evolving Technology for the Modulation of Gene Expression in Human Disease, J Am Coll Surg, Jul. 2000, vol. 191, No. 1, pp. 93-105.*
Crooke, Antisense Research and Application, Chapter 1, Springer-Verlag, New York, 1998.*
Krause, Chromatin structure and function: the heretical path to an RNA transcription factor, 1996, Biochem. Cell Biol., 74(5), pp. 623-632.*
Luo et al., C-Myc Deregulation During Transformation Induction: Involvement of 7SK RNA. 1997. Journal of Cellular Biochemistry, vol. 64, pp. 313-327.*
Nguyen et al., 7SK small nuclear RNA binds and inhibits the activity of CDK9/cyclin T complexes, 2001, Nature, vol. 414, pp. 322-325.*
Bieniasz et al., Recruitment of cyclin T1/P-TEFb to an HIV type 1 long terminal repeat promoter proximal RNA target is both necessary and sufficient for full activation of transcription, 1999, Proc. Natl. Acad. Sci., vol. 96, pp. 7791-7796.*
Wada et al., Evidence that P-TEFb alleviates the negative effect of DSIF on RNA Polymerase II-dependent transcription in vivo, 1998, The EMBO Journal, vol. 17, No. 24, pp. 7395-7403.*

\* cited by examiner

*Primary Examiner*—James Schultz
*Assistant Examiner*—Amy H. Bowman
(74) *Attorney, Agent, or Firm*—Richard Aron Osman

(57) ABSTRACT

A method for altering transcription in a cell comprising an amount of active CDK9/cyclin, comprises the steps of: (a) introducing in the cell an agent which modulates the amount of active CDK9/cyclin in the cell, and thereby alters transcription in the cell, wherein the agent comprises an RNA selected from the group consisting of an RNA aptamer that specifically binds CDK9/cyclin, a CDK9/cyclin-binding domain of 7SK RNA, a 7SK RNA-binding antisense 7SK RNA domain, and a 7SK RNA-specific RNAi, and (b) detecting a resultant altering of transcription in the cell.

Methods for screening for an agent which modulates 7SK RNA-CDK9/cyclin binding generally comprise the steps of (a) incubating a mixture of 7SK RNA, CDK9/cyclin and a candidate agent under conditions wherein but for the presence of the agent, the 7SK RNA and CDK9/cyclin engage in a reference binding; and (b) detecting an agent-biased binding of the 7SK RNA to the CDK9/cyclin.

12 Claims, No Drawings

7SK RNA REGULATED TRANSCRIPTION

This invention was made with Government support under Grant No. AI41757 awarded by the National Institutes of Health. The Government has certain rights in this invention.

INTRODUCTION

1. Field of the Invention

The field of the invention is 7SK small nuclear RNA regulated gene transcription.

2. Background of the Invention

The human positive transcription elongation factor P-TEFb, consisting of a CDK9/cyclin T1 heterodimer, functions as both a general and an HIV-1 Tat-specific transcription factor (1,2). P-TEFb activates transcription by phosphorylating RNA polymerase (Pol) II, leading to the formation of processive elongation complexes. As a Tat cofactor, P-TEFb stimulates HIV-1 transcription by interacting with Tat and the transactivating responsive (TAR) RNA structure located at the 5' end of the nascent viral transcript (3). We identified 7SK (SEQ ID NO:1), an abundant and evolutionarily conserved small nuclear RNA (sn-RNA) of previously unknown function (4,5), as a specific P-TEFb-associated factor. 7SK inhibits general and HIV-1 Tat-specific transcriptional activities of P-TEFb in vivo and in vitro by inhibiting the kinase activity of CDK9 and preventing recruitment of P-TEFb to the HIV-1 promoter (Yang et al, Nature 414, 317–322, 2001; see also, Nguyen et al., Nature 414, 322–325, 2001; Blencowe, Current Biol 12, R147–9, 2002). 7SK is efficiently dissociated from P-TEFb by treatment of cells with ultraviolet irradiation and actinomycin D. As these two agents have been shown to significantly enhance HIV-1 transcription and phosphorylation of Pol II (6,7,8), our data provide a mechanistic explanation for their stimulatory effects. The disclosed inventions exploit our finding that the 7SK/P-TEFb interaction serves as a principal control point for the induction of cellular and HIV-1 viral gene expression, particularly during stress-related responses.

SUMMARY OF THE INVENTION

The invention provides methods and compositions for regulating transcription. The inventors have found that they can modulate transcription by modulating sequestration of P-TEFb (a CDK9/cyclin complex) by RNA. Hence, the invention provides methods for altering transcription in a cell comprising an amount of active CDK9/cyclin, comprising the steps of: (a) introducing in the cell an agent which modulates the amount of active CDK9/cyclin in the cell, and thereby alters transcription in the cell, wherein the agent comprises an RNA selected from the group consisting of an RNA aptamer that specifically binds CDK9/cyclin, a CDK9/cyclin-binding domain of 7SK RNA, a 7SK RNA-binding antisense 7SK RNA domain, a 7SK RNA-specific ribozyme, and a 7SK RNA-specific RNAi, and (b) detecting a resultant altering of transcription in the cell.

Depending on the selected agent, the method can decrease the amount of active CDK9/cyclin in the cell and thereby reduce said transcription, or increase the amount of active CDK9/cyclin in the cell and thereby increase said transcription. For example, in particular embodiments, (a) the RNA is an RNA aptamer that specifically binds CDK9/cyclin, decreases the amount of active CDK9/cyclin in the cell, and thereby reduces said transcription; (b) the RNA comprises a CDK9/cyclin-binding domain of 7SK RNA, decreases the amount of active CDK9/cyclin in the cell, and thereby reduces said transcription; (c) the RNA comprises a 7SK RNA-binding antisense 7SK RNA domain, increases the amount of active CDK9/cyclin in the cell, and thereby increases said transcription; (d) the RNA comprises a 7SK RNA-specific ribozyme, increases the amount of active CDK9/cyclin in the cell, and thereby increases said transcription; or (e) the RNA comprises a 7SK RNA-specific RNAi, increases the amount of active CDK9/cyclin in the cell, and thereby increases said transcription.

A wide variety of transcriptions may be targeted; in particular embodiments, the transcription is (a) a recombinant protein transcription; (b) an LTR promoter-controlled transcription; or (c) HIV transcription.

The invention also provides methods for screening for an agent which modulates 7SK RNA-CDK9/cyclin binding. In general, these methods comprise the steps of (a) incubating a mixture of 7SK RNA, CDK9/cyclin and a candidate agent under conditions wherein but for the presence of the agent, the 7SK RNA and CDK9/cyclin engage in a reference binding; and (b) detecting an agent-biased binding of the 7SK RNA to the CDK9/cyclin, wherein a difference between the reference binding and the agent-biased binding indicates that the agent modulates 7SK RNA-CDK9/cyclin binding.

Essentially any candidate agent or library of agents may be screened; in particular embodiments, the agent comprises (a) an RNA aptamer that specifically binds CDK9/cyclin; (b) a CDK9/cyclin-binding domain of 7SK RNA; (c) a 7SK RNA-binding antisense 7SK RNA domain; (d) a 7SK RNA-specific ribozyme; or (e) a 7SK RNA-specific RNAi. In addition, a wide variety of formats may be used; in particular embodiments, the binding is detected (a) directly in a co-precipitation binding assay; (b) directly in a solid-phase binding assay; (c) indirectly in a transcriptional readout assay; or (d) indirectly in a viral replication assay. Furthermore, a wide variety of mixtures may be used, depending on the selected assay format; for example, the mixture may be a cell-free lysate or solution, or a cell in vitro or in situ.

DETAILED DESCRIPTION OF PARTICULAR EMBODIMENTS OF THE INVENTION

Our general method for altering transcription in a cell comprising an amount of transcriptionally active CDK9/cyclin, comprises introducing in the cell an agent which modulates the amount of active CDK9/cyclin in the cell by modulating the amount of CDK9/cyclin bound and sequestered by 7SK RNA, and thereby alters CDK9/cyclin-dependent transcription in the cell. Active CDK9/cyclin is unsequestered by 7SK RNA and provides demonstrable kinase and transcriptional activity, as shown below. Accordingly, subject agents simulate, promote or inhibit 7SK RNA binding to CDK9/cyclin. Agents include regulators of endogenous 7SK RNA expression, exogenous 7SK RNA molecules, agonistic (e.g. simulatory) or antagonistic (e.g. dominant negative) domains thereof, 7SK RNA-specific ribozymes, RNAi's and antisense RNAs, and agents identified or characterized in the subject 7SK RNA-CDK9/cyclin binding assays. In particular embodiments, the agent comprises, and preferably consists or consists essentially of, an RNA selected from the group consisting of an RNA aptamer that specifically binds CDK9/cyclin, a CDK9/cyclin-binding domain of 7SK RNA, a 7SK RNA-binding antisense 7SK RNA domain, a 7SK RNA-specific ribozyme, and a 7SK RNA-specific RNAi.

Depending on the selected agent, the method can decrease the amount of active CDK9/cyclin in the cell and thereby reduce said transcription, or increase the amount of active CDK9/cyclin in the cell and thereby increase said transcription. For example, domains and derivatives of 7SK RNA, including SELEX-derived aptamers, can bind CDK9/cyclin as an agonist and decrease the amount of active CDK9/cyclin in the cell, or as an antagonist, interfering with endogenous 7SK RNA binding while not interfering with CDK9/cyclin-dependent transcription.

Hence, in particular embodiments, the selected agent promotes CDK9/cyclin sequestration by promoting or stabilizing binding to endogenous 7SK RNA, or providing additional 7SK RNA or domains or derivatives thereof which bind CDK9/cyclin and thereby inhibit CDK9/cyclin-dependent transcription. For example, we identified a variety of distinct binding promoters and stabilizers in our 7SK RNA-CDK9/cyclin binding assays (below). Similarly, by deletion and mutation analysis, we identified and characterized a number of CDK9/cyclin binding domains of RNAs, including domain mutants, including recombined 7SK RNA domains, sufficient to bind and thereby inhibit CDK9/cyclin-dependent transcription. Table 1 provides a number of exemplary 7SK RNA domains sufficient to bind CDK9/cyclin and thereby inhibit CDK9/cyclin-dependent transcription. 7SKD1 for example, is an internal deletion, wherein nucleotides 161–300 of native 7SK RNA (SEQ ID NO: 1) are deleted. By convention, RNA sequences are presented herein by their corresponding DNA sequences.

TABLE 1

Exemplary 7SK RNA domains sufficient to bind CDK9/cyclin and thereby inhibit CDK9/cyclin-dependent transcription.

| RNA | Structure | CDK9/cyclin binding | Transcription Inhibition |
|---|---|---|---|
| 7SKD1 | SEQ ID NO: 2 | +++ | +++ |
| 7SKD2 | SEQ ID NO: 3 | +++ | +++ |
| 7SKD3 | SEQ ID NO: 4 | +++ | +++ |
| 7SKD4 | SEQ ID NO: 5 | +++ | +++ |
| 7SKM2 | SEQ ID NO: 6 | +++ | +++ |
| 7SKM3 | SEQ ID NO: 7 | +++ | +++ |
| 7SKM2 | SEQ ID NO: 8 | +++ | +++ |
| 7SKM3 | SEQ ID NO: 9 | +++ | +++ |

We selected several CDK9/cyclin-binding domains of 7SK RNA for SELEX (systematic evolution of ligands by exponential enrichment; Turek et al. Science 249, 505–10, 1990; Martell et al., Mol Ther. 2002 July; 6(1):30–4) to generate a panel of CDK9/cyclin-specific RNA aptamers. Our exemplary protocol for preparing SELEX-derived RNA aptamers specific for 7SK RNA is similar to that described in Joshi et al. J Virol 2002 July; 76(13):6545–57. Briefly, to assay HIV-1 transcriptional inhibition, aptaniers are expressed with flanking, self-cleaving ribozymes to generate aptamer RNA transcripts with minimal flanking sequences. From these we select aptamers based on binding constants (K(d)) and the degree of inhibition of HIV transcription in vitro (50% inhibitory concentration [IC(50)]). These aptamers are each stably expressed in 293T cells followed by transfection of a molecular clone of HIV. Selected aptamers demonstrate consistently reduced viral transcription and particle production.

Subsequently, we designed luciferase transcriptional reporter assays to identify a panel of transcriptional regulators of 7SK RNA expression. In our assay, 100 ng 7SK RNA promoter (e.g. U.S. Pat. No. 5,624,803; Boyd et al., Mol Biol. Nov. 10, 1995;253(5):677–90; Boyd et al., Gene 2000 April 18 ;247(1–2):33–44)—luciferase reporter constructs are transfected into HeLa cells pre-seeded at 2×105 cells per well in a 6-well dish. After 44 hr incubation, candidate transcriptional regulators are provided to discrete cultures in logarithmic dosages at hourly time points. After 48 hr total incubation, cell lysates are analysed for luciferase activity. Trans-acting candidates are subject to CDK9/cyclin binding and HIV-1 transcription assays (supra). Table 2 shows the effect of exemplary transcriptional regulators on 7SK RNA gene expression, CDK9/cyclin-specific binding and specific inhibition of CDK9/cyclin-dependent transcription.

TABLE 2

The effect of exemplary transcriptional regulators on 7SK RNA gene expression, CDK9/cyclin-specific binding and specific inhibition of CDK9/cyclin-dependent transcription ---, and +++ indicate significant decreases and increases, respectively over three experiments.

| Transcriptional Regulator | Luciferase Expression | CDK9/cyclin binding | Transcription Inhibition |
|---|---|---|---|
| ADH368 | −45% | --- | --- |
| ADH042 | −83% | --- | --- |
| ADH947 | −27% | --- | --- |
| ADH506 | +59% | +++ | +++ |
| ADH487 | +662% | +++ | +++ |
| ADH122 | +134% | +++ | +++ |

We also demonstrated our method with 7SK RNA-binding antisense 7SK RNA domains, with and without supplemental RNase H cleavage. In our initial experiments, antisense and scrambled oligonucleotides specifically targeting various 7SK RNA regions were transfected into HeLa cells together with an HIV-1 LTR luciferase construct. We found that antisense 7SK RNA domains could significantly increase transcription, and that these increases correlated with their ability to inhibit 7SK-CDK9/cyclin binding.

Our 7SK RNA-specific RNAi and 7SK RNA-specific ribozyme assays are constructed similarly. 7SK RNA-specific RNAi (Elbashir et al,. Methods 2002 February;26(2): 199–213; Hannon, 2002, Nature 418, 244 51), and trans-cleaving, 7SK RNA-specific ribozymes (Lyngstadaas, 2001, Crit Rev Oral Biol Med 12(6):469–78; Doudna et al., 2002 Nature 418, 222–228) specifically targeting various 7SK RNA regions are transfected into HeLa cells together with an HIV-1 LTR luciferase construct. Results indicate that our 7SK RNA-specific RNAi and 7SK RNA-specific ribozymes can significantly increase transcription, and that these increases correlate with their ability to inhibit 7SK-CDK9/cyclin binding. Similar results are obtained using retroviral vectors to introduce expression cassettes for 7SK RNA-specific ribozymes into CD4+lymphocytes or CD34+haematopoeietic precursors ex vivo, isolated from infected patients. To enhance therapeutic persistence, nuclease resistant synthetic ribozymes may be used (e.g. Usman et al., J Clin Invest 106, 1197–1202, 2000).

A wide variety of transcriptions may be targeted by our methods. For example, the method is particularly suited to increasing target viral or recombinant protein transcription. While lentivirus LTR-promoted transcription is particularly sensitive, CDK9/cyclin is often transcriptionally limiting in mammalian cells. Hence, the method may be used to increase the yield of proteins recombinantly expressed in mammalian cells, particularly under lentivirus LTR promoters. In a particular application, the methods are used to therapeutically increase HIV transcription, accelerating viremia and host immune responsiveness.

Alternatively, by using agents which promote CDK9/cyclin sequestration by promoting or stabilizing binding to endogenous 7SK RNA, or providing additional 7SK RNA or domains or derivatives thereof which bind CDK9/cyclin and thereby inhibit CDK9/cyclin-dependent transcription, the methods may be used to decrease target viral or recombinant protein transcription. Targets of transcriptional inhibition are generally pathogenic transcriptions, including expression of pathogenic viral and host genes.

In many applications, particularly for increasing expression of recombinant proteins, the target cells are in vitro. This aspect of the invention is useful for providing enhance expression of virtually any recombinant protein, particularly commercial and therapeutic proteins. For example, we modified a commercial protocol (Cosgrove et al., Protein Expr Purif 1995 December;6(6):789–98) for large-scale production of insulin receptor by incubating with a high-affinity CDK9/cyclin binding, SELEX-derived 7SK RNA aptamer. Our aptamer is further protected from RNase degradation by condensation with the polycationic peptide protamine, which also promotes intracellular delivery. Briefly, ectodomain of the exon 11+ form of the human insulin receptor (hIR) is expressed in the mammalian cell secretion vector pEE6.HCMV-GS, containing the glutamine synthetase gene. Following transfection of the hIR ectodomain gene into Chinese hamster ovary (CHO-K1) cells, clones are isolated by selecting for glutamine synthetase expression with methionine sulphoximine. The expression levels of ectodomain are subsequently increased by gene amplification. Production is scaled up using a 40-liter airlift fermenter in which the transfected CHO-K1 cells were cultured on microcarrier beads in the presence of our 7SK RNA aptamer, initially in medium containing 10% fetal calf serum (FCS). By continuous perfusion of serum-free medium supplemented with aptamer into the bioreactor, cell viability is maintained during reduction of FCS, which enabled soluble hIR ectodomain to be harvested for at least 22 days. Our results demonstrate the successful production and purification of hIR ectodomain by processes amenable to large scale-up.

In other embodiments, the target cell is in situ, particularly a cell of a patient determined to be in need of specific transcriptional modulation, particularly one determined to be subject to pathogenic transcription, particularly of protein pathogenic or expressed at a pathogenic level in the host. The patient is typically a human patient, but also includes animal, particularly mammalian patients such as dogs and cats encountered in veterinary applications, and rats and mice encountered in biomedical research applications. Hence, the need for transcriptional modulation will generally originate with the patient, but may also be that imposed by the biomedical researcher. In a particular embodiment, the patient is a human predetermined to be in medical need of transcriptional modulation, more particularly, a patient suffering from a lentivirus, particularly an HIV infection.

Protocols for delivering the agent and effective dosages are known in the art and/or readily determined empirically by those skilled in the art guided by the selected agent and the present disclosure. As noted and exemplified herein, a wide variety of alternative agents may be employed, guided by efficacy, physiological compatibility and convenience. For example, a variety of applicable delivery protocols have been shown to effectively deliver therapeutic RNA agents to mammalian cells and animals, see Sullenger et al., 2002, Nature 418, 252–58, and references therein. For example, expression cassette SELEX greatly facilitates the use of aptamers for a variety of gene therapy applications. Martell et al., Mol Ther. 2002 July;6(1):30–4; and for various protocols for therapeutic aptamer delivery, see, White et al., 2000, J Clin Invest 106, 929–34; Hicke et al., 2000, J Clin Invest 106, 923–28.

In a particular embodiment, retroviral vectors are used to mediate transfer of 7SK RNA-specific ribozyme and a control $neo^R$ gene into CD4$^+$ T-cells selected from apheresis samples of HIV-infected patients. In patients analyzed to date, transduced cells of each population (ribozyme and control) were found up to 10 months post-infusion. A related study using an HIV-specific ribozyme in CD34+ cells found multilineage gene presence after at 3 months (Amado et al., 6$^{th}$ Conf Retroviruses Opportunistic Infections, Chicago, Ill., Abstr #17, 1999). Another study utilized an anti-HIV-1 tat and rev double hammerhead in a similar CD34$^+$ cell study. Long-term bone marrow cultures of ribozyme transduced cells showed protection from HIV challenge compared to control-transduced cells. In half of patients observed for at least 12 months, vector sequences were detectable by DNA PCR in PBMC and/or marrow at 6 months.

The agents are typically administered in the form of a pharmaceutical composition comprising at least one recited agent and a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions. Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The dosage forms may include a variety of other ingredients, including binders, solvents, bulking agents, plasticizers etc. Preferred agents are orally administrable to human patients, meaning they are both safe and effective when orally administered. The above described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose. The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

Our methods generally also comprise the step of detecting or confirming a resultant altering of transcription in the target cell. Transcriptional modulation may be detected in any convenient manner, including directly, such as by reporter expression, or indirectly, such as by a target transcription dependent change in host cell or animal physiology (e.g. viremia, pathology, or other ultimate indication of transcriptional change).

The invention also provides methods for screening for an agent which modulates 7SK RNA-CDK9/cyclin binding. In general, these methods comprise the steps of (a) incubating a mixture of 7SK RNA, CDK9/cyclin and a candidate agent under conditions wherein but for the presence of the agent, the 7SK RNA and CDK9/cyclin engage in a reference binding; and (b) detecting an agent-biased binding of the 7SK RNA to the CDK9/cyclin, wherein a difference between the reference binding and the agent-biased binding indicates that the agent modulates 7SK RNA-CDK9/cyclin binding. Essentially any candidate agent or library of agents may be screened in any of the cell or animal systems described or cited herein, that provide a measure of 7SK RNA-CDK9/cyclin binding, CDK9/cyclin kinase activity, CDK9/cyclin-dependent transcription, etc. In a particular embodiment, we used an in vitro, cell-based transcriptional reporter assay to identify a variety of distinct 7SK RNA-CDK9/cyclin binding promoters and stabilizers (Table 3).

TABLE 3

Exemplary 7SK RNA - CDK9/cyclin binding promoters and stabilizers.

| Binding promoter | CDK9/cyclin binding | Luciferase Expression | Transcription Inhibition |
| --- | --- | --- | --- |
| ALM726 | +++ | +107% | +++ |
| ALM488 | +++ | +372% | +++ |
| ALM045 | +++ | +94% | +++ |
| ALM362 | +++ | +405% | +++ |
| ALM157 | +++ | +223% | +++ |
| ALM283 | +++ | 3.5 | +++ |

Exemplary Experimental Protocols

To identify nuclear factors that can interact with and regulate the activity of P-TEFb, we affinity purified Flag-tagged CDK9 and its associated factors from the nuclear extract of an engineered HeLa cell line (F1C2 cells) that stably expressed CDK9-Flag (9). Analysis of the purified material by silver staining detected cyclin T1 and a novel band with a relative molecular mass of 110,000 (Mr 110K) derived from F1 C2 but not the parental HeLa cells. Coomassie blue could not stain the 110K band, and the yellowish, silver-stained color was different from that of the brown color typical of proteins, indicating that the band may not be a protein. Indeed, treatment of the affinity-purified CDK9-Flag preparation with RNase A, but not DNase I, eliminated the 110K band, indicating that it may contain a CDK9-associated RNA molecule.

RNA was extracted from the CDK9-Flag preparation and analysed on a denaturing gel with small RNAs recovered from HeLa nuclear extract as markers. The identities of some of these HeLa RNAs were pre-determined by oligonucleotide-directed RNase H digestion (10). The CDK9-Flag preparation contained a single RNA species that comigrated with the 7SK RNA, comprising 330 nucleotides, in HeLa extract. On transcription by RNA Pol III, the mammalian 7SK RNA is an abundant (approximately $2 \times 10^5$ per cell) and evolutionarily conserved snRNA of unknown function (4,11). Using full-length 7SK antisense RNA as a probe, northern hybridization was performed to confirm that the CDK9-associated 110K RNA was 7SK. Sequencing of the complementary DNA copy of this RNA revealed a complete match with the published 7SK sequences (12).

To investigate the role of 7SK in transcription, it was quantitatively removed from HeLa nuclear extract using an immobilized 2'-O-methyl (2'-OMe) RNA oligonucleotide complementary to an exposed region in 7SK (residues 221–241) (4). Notably, the 7SK small nuclear ribonucloprotein particle (snRNP) associated with the 2'-OMe RNA beads contained both cyclin T1 and CDK9, indicating an association of 7SK with the CDK9/cyclin T1 heterodimer in HeLa nuclear extract. Approximately twice the amount of cyclin T1 and CDK9 was detected in the mock-depleted extract than in the extract that was depleted of 7SK, indicating that about 50% of P-TEFb may be stably associated with 7SK.

We next compared the abilities of the mock- and 2'-OMe RNA-depleted HeLa nuclear extracts to transcribe templates pSV40EP-G400 and pHIVTAR-G100 (13) in the same reaction. Removal of 7SK and its associated P-TEFb had no effect on transcription proximal to the promoter of the 400-nucleotide G-less cassette (G400), which was driven by the SV40 early promoter, or on transcription distal to the promoter of a G100 cassette, driven by the HIV-1 promoter; furthermore, there was no effect on Tat activation of HIV-1 transcription. Thus, the P-TEFb bound to 7SK did not contribute to the transcriptional activity of HeLa nuclear extract.

If the P-TEFb bound to 7SK is inactive in transcription, we asked whether this might be due to 7SK having an inhibitory effect on the function of P-TEFb. To disrupt 7SK, oligonucleotide-directed RNase H digestion (10) of 7SK was performed in the nuclear extract of F1C2 cells. Treatment with 221-241A—an antisense deoxyoligonucleotide targeted against 7SK-but not a control oligonucleotide, caused cleavage of full-length 7SK (330 nucleotides) into two fragments of approximately 220 and 90 nucleotides, respectively. The integrity of the targeted region (nucleotides 221–241) appeared to be critical for the binding of 7SK to P-TEFb, as very little of the cleaved 7SK fragments were associated with the affinity-purified CDK9-Flag/cyclin T1. Thus, treatment with 221-241A effectively created more P-TEFb that was not bound to 7SK (free P-TEFb), in the extract. Compared with both untreated and control oligonucleotide-treated extracts, the extract treated with 221-241A consistently yielded 2-3-fold more basal and Tat-activated HIV-1 transcription from templates pHIV+TAR-G400 (which contained the wild-type TAR element) and pHIVTAR-G100 (with a mutant TAR) (13). Given that only about 50% of P-TEFb associated with 7SK, the 2-3-fold increase in transcription was significant, and it indicated that 7SK was suppressing the transcriptional activity of P-TEFb in vitro.

When 221-241A or a scrambled oligonucleotide, 221-241S, was cotransfected with CDK9-Flag into HeLa cells, only 221-241A significantly reduced the binding of 7SK to CDK9-Flag, effectively creating more free P-TEFb in the cell. To determine whether 7SK also suppresses P-TEFb activity in vivo, the effect of 221-241A on the abilities of various promoters to transcribe a luciferase reporter gene was examined. Transfection of 221-241A, but not 221-241S, into HeLa cells increased transcription from all promoters tested, with the largest increase (roughly 9.5-fold) displayed by the HIV-1 long terminal repeat (LTR). Smaller increases were displayed by the SV40 early promoter, and the (Gal4) 5-thymidine kinase promoter, the transforming growth factor responsive promoter p3TP. Similar results were also obtained in several other cell lines of diverse origins. Finally, transfection of 221-241A into HeLa cells increased both basal and Tat-activated HIV-1 transcription. These experiments and the above in vitro transcriptional analyses reveal a general inhibitory effect of 7SK on P-TEFb transcriptional activity. Notably, HIV-1 LTR seems to be most sensitive to this inhibition, which is reasonable because it is regulated mainly at the stage of elongation and requires P-TEFb for both basal and Tat-activated transcription (1,2).

In addition to the region targeted by 221-241A, two other regions of 7SK (residues 11–31 and 95–114) are also potentially accessible to oligonucleotide-directed RNase H cleavage (4,14). Antisense and scrambled deoxyoligonucleotides specifically targeting these two regions were therefore transfected into HeLa cells together with an HIV-1 LTR luciferase construct. Compared with 221-241A, which increased significantly HIV transcription, a smaller increase was observed with the antisense oligonucleotide 95-114A, and no increase with oligonucleotide 11-31A was observed. The abilities of the three antisense oligonucleotides to increase transcription correlated exactly with their abilities to induce 7SK cleavage and to disrupt the interaction between 7SK and P-TEFb in the nuclear extract, further documenting the inhibitory effect of 7SK on the transcriptional activity of P-TEFb.

7SK could inhibit the activity of P-TEFb by suppressing the kinase activity of CDK9/cyclin T1. Affinity-purified CDK9-Flag and its associated factors were divided into two halves, incubated respectively with RNase A and DNase I, and tested in kinase reactions containing purified RNA Pol II as a substrate (9). RNase A degraded the CDK9-Flag-associated 7SK, and increased the kinase activity of CDK9-Flag by 3-4-fold, as seen by its increased autophosphorylation and phosphorylation of Pol II. This increase was significant given that only about 50% of the purified CDK9-Flag/cyclin T1 was associated with 7SK. In addition to RNase A, RNase H cleavage of 7SK directed by 221-241A also increased the kinase activity of CDK9. To analyse more specifically the activity of P-TEFb bound to 7SK, this complex was affinity purified from HeLa nuclear extract using the 7SK antisense 2'-OMe RNA beads. Eluted with a displacement deoxyoligonucleotide (15), the P-TEFb bound to 7SK was divided into three equal portions, incubated respectively with RNase A, DNase I or buffer alone, and analysed in kinase reactions. Once again, degradation of 7SK by RNase A significantly increased the kinase activity of CDK9, revealing the inhibitory action of 7SK on CDK9/cyclin T1 kinase.

P-TEFb can be recruited to the pre-initiation complex (PIC) at the HIV-1 promoter and then travel with the elongating Pol II (16,17). The mechanism of recruitment is unclear although the interaction of cyclin T1 with the hypophosphorylated Pol II (18) could be responsible. To study the effect of 7SK on the association of P-TEFb with PIC, an immobilized HIV-1 promoter was incubated with F1C2 nuclear extract to isolate the promoter-bound P-TEFb (16,17). Northern blotting was performed to compare the level of 7SK associated with the promoter-bound P-TEFb with that in the total P-TEFb affinity purified from the nuclear extract. When normalized by their cyclin T1 and CDK9 levels, the promoter-bound P-TEFb showed no 7SK, whereas abundant 7SK existed in the total P-TEFb preparation, indicating that 7SK prevented the binding of P-TEFb to the HIV-1 promoter in vitro. To verify this in vivo, a chromatin immunoprecipitation (CHIP) (19) assay was performed to examine the interaction of P-TEFb with an integrated HIV-1 promoter in HeLa cells. Cells were cotransfected with CDK9-Flag and either 221-241A or 221-241S. As shown above, transfected 221-241A disrupted the 7SK/P-TEFb interaction and increased HIV-1 transcription. Notably, it also increased the association of CDK9-Flag with the HIV-1 promoter in these cells. Thus, the 7SK-P/TEFb interaction not only inhibited the kinase activity of P-TEFb, but also blocked the recruitment of P-TEFb to the HIV-1 promoter.

Certain agents that elicit SOS-like stress responses in mammalian cells can markedly enhance HIV-1 transcription in a manner analogous to prophage induction in *Escherichia coli* (6–8,20,21). For instance, treatment of HeLa cells with ultraviolet irradiation or low levels of the global transcription inhibitor actinomycin D enhances HIV-1 transcription to levels similar to those obtained by Tat (6,8). Notably, these stimulatory effects seemed to be caused by an enhanced phosphorylation of Pol II, probably by the CDK9/cyclin T1 kinase (6). In light of these observations, we investigated the effect of ultraviolet irradiation and actinomycin D on the 7SK/P-TEFb interaction in nuclear extracts of the treated F1C2 cells. Consistent with their enhancement of HIV-1 transcription and Pol II phosphorylation, both agents significantly reduced the amount of 7SK associated with the affinity-purified CDK9-Flag. Neither the level of total 7SK in the nuclear extract nor the CDK9/cyclin T1 interaction was affected. Actinomycin D is known to intercalate into duplex DNA and perhaps also RNA; however, direct incubation of this drug with nuclear extract did not disrupt the 7SK/P-TEFb interaction, ruling out a direct effect. As for ultraviolet irradiation, 7SK was dissociated from P-TEFb as early as 15–30 min after treatment, long before any signs of apoptosis appeared. Thus, stress signals such as ultraviolet irradiation and actinomycin D can cause fast and efficient 7SK dissociation from P-TEFb, which explains their positive effects on HIV-1 transcription and Pol II phosphorylation.

Constructs and stable CDK9-Flag-expressing cell line. In vitro transcription template pSV40EP-G400 was generated by cloning a 400-nucleotide G-less cassette (G400)(13) into the HindII and EcoRV sites downstream of the SV40 early promoter in pGL-2 (Promega). We performed in in vitro transcription assay as described (13). To generate the F1C2 cell line expressing CDK9-Flag, HeLa cells were stably transfected with pBabe-puro-CDK9-Flag, which expresses Flag-tagged CDK9 and confers puromycin resistance. We selected clone F1C2 because CDK9-Flag is expressed at a similar level as the endogenous CDK9. CDK9-Flag and its associated factors were affinity purified from F1C2 nuclear extract using anti-Flag agarose beads (Sigma). After extensive washes with buffer D (20 mM HEPES, pH 7.9, 15% glycerol, 0.2 mM EDTA, 1 mM dithiothreitol, 0.5 mM phenylmethyl sulphonyl fluoride) containing 0.4 M KCl and 0.2% NP40, the materials were eluted by Flag peptide as described (9).

Transfection of cells with deoxyoligonucleotides. For luciferase assays, HeLa cells were seeded at 2×105 cells per well in a 6-well dish one day before transfection. Using the Lipofectamine-Plus Kit (Invitrogen), cells were cotransfected with 100 ng of the indicated luciferase reporter constructs, 2 ug high-performance liquid chromatography-pure deoxyoligonucleotides, and 20 ng Tat-expressing construct when indicated. Cell lysates were analysed for luciferase activity at 48 h after transfection. For chromatin immunoprecipitation assays (CHIP), a total of 6×106 HeLa cells containing an integrated HIV-1 LTR was seeded one day before transfection into five 10-cm dishes. Cells were cotransfected with 12 ug per dish of the indicated oligonucleotides and 4 ug per dish of a construct expressing CDK9-Flag. At 36 h after transfection, cells were processed for crosslinking and CHIP with anti-Flag agarose beads as described (19). The HIV-1 promoter region between −168 and +82 was amplified by polymerase chain reaction from the precipitated chromatin.

Depletion, purification and cleavage of 7SK. Depletion of the 7SK RNP from HeLa nuclear extract was performed as described (4) with some modifications. Briefly, 300 ul HeLa extract in buffer D plus 0.1 M KCl, 0.05% NP40 and 0.2 U ul-1 RNasin was incubated at 30° C. for 30 min with 1.8 uM of the biotinylated antisense 2'-O-methyl RNA oligonucleotide that is complementary to a region in 7SK from nucleotide 221 to 241. The reaction mixture was then incubated for 1 h at 4° C. with streptavidin agarose beads (Sigma). After repeating the procedure twice, the beads were washed with buffer D containing 0.4 M KCl and 0.2% NP40, and the associated 7SK RNP was analysed. To elute 7SK RNP from the beads, we used a 2.5-fold excess displacement deoxyoligonucleotide in buffer D (0.1 M KCl). We performed oligonucleotide-directed RNase H cleavage of 7SK as described (10).

REFERENCES

1. Jones, K. A. Taking a new TAK on Tat transactivation. Genes Dev. 11, 2593–2599 (1997).
2. Price, D. H. P-TEFb, a cyclin-dependent kinase controlling elongation by RNA polymerase II. Mol. Cell. Biol. 20, 2629–2634 (2000).
3. Wei, P., Garber, M. E., Fang, S. M., Fischer, W. H. & Jones, K. A. A novel CDK9-associated C-type cyclin interacts directly with HIV-1 Tat and mediates its high-affinity, loop-specific binding to TAR RNA. Cell 92, 451–462 (1998).
4. Wassarman, D. A. & Steitz, J. A. Structural analyses of the 7SK ribonucleoprotein (RNP), the most abundant human small RNP of unknown function. Mol. Cell. Biol. 11, 3432–3445 (1991).
5. Zieve, G. & Penman, S. Small RNA species of the HeLa cell: metabolism and subcellular localization. Cell 8, 19–31 (1976).
6. CassΘ, C., Giannoni, F., Nguyen, V. T., Dubois, M. F. & Bensaude, O. The transcriptional inhibitors, actinomycin D and -amanitin, activate the HIV-1 promoter and favor phosphorylation of the RNA polymerase II C-terminal domain. J. Biol. Chem. 274, 16097–16106 (1999).
7. Kumar, S. et al. Activation of the HIV-1 long terminal repeat by cytokines and environmental stress requires an active CSBP/p38 MAP kinase. J. Biol. Chem. 271, 30864–30869 (1996).
8. Valerie, K. et al. Activation of human immunodeficiency virus type 1 by DNA damage in human cells. Nature 333, 78–81 (1988).
9. Zhou, Q., Chen, D., Pierstorff, E. & Luo, K. Transcription elongation factor P-TEFb mediates Tat activation of HIV-1 transcription at multiple stages. EMBO J. 17, 3681–3691 (1998).
10. Black, D. L., Chabot, B. & Steitz, J. A. U2 as well as U1 small nuclear ribonucleoproteins are involved in premessenger RNA splicing. Cell 42, 737–750 (1985).
11. Zieve, G., Benecke, B. J. & Penman, S. Synthesis of two classes of small RNA species in vivo and in vitro. Biochemistry 16, 4520–4525 (1977).
12. Murphy, S. et al. DNA sequences complementary to human 7 SK RNA show structural similarities to the short mobile elements of the mammalian genome. J. Mol. Biol. 177, 575–590 (1984).
13. Zhou, Q. & Sharp, P. A. Novel mechanism and factor for regulation by HIV-1 Tat. EMBO J. 14, 321–328 (1995).
14. Luo, Y., Kurz, J., MacAfee, N. & Krause, M. O. C-myc deregulation during transformation induction: involvement of 7SK RNA. J. Cell. Biochem. 64, 313–327 (1997).
15. Schnapp, G., Rodi, H. P., Rettig, W. J., Schnapp, A. & Damm, K. One-step affinity purification protocol for human telomerase. Nucleic Acids Res. 26, 3311–3313 (1998).
16. Ping, Y. H. & Rana, T. M. Tat-associated kinase (P-TEFb): a component of transcription preinitiation and elongation complexes. J. Biol. Chem. 274, 7399–7404 (1999).
17. Zhou, M. et al. Tat modifies the activity of CDK9 to phosphorylate serine 5 of the RNA polymerase II carboxyl-terminal domain during human immunodeficiency virus type 1 transcription. Mol. Cell. Biol. 20, 5077–5086 (2000).
18. Fong, Y. W. & Zhou, Q. Relief of two built-in autoinhibitory mechanisms in P-TEFb is required for assembly of a multicomponent transcription elongation complex at the human immunodeficiency virus type 1 promoter. Mol. Cell. Biol. 20, 5897–5907 (2000).
19. Boyd, K. E., Wells, J., Gutman, J., Bartley, S. M. & Farnham, P. J. c-Myc target gene specificity is determined by a post-DNA binding mechanism. Proc. Natl Acad. Sci. USA 95, 13887–13892 (1998).
20. Kretz-Remy, C. & Arrigo, A. P. The kinetics of HIV-1 long terminal repeat transcriptional activation resemble those of hsp70 promoter in heat-shock treated HeLa cells. FEBS Lett. 353, 339–344 (1994).
21. Vlach, J. et al. Induction of Sp1 phosphorylation and NF-B-independent HIV promoter domain activity in T lymphocytes stimulated by okadaic acid. Virology 208, 753–761 (1995).

The foregoing descriptions of particular embodiments and examples are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification and all references cited therein are herein incorporated by reference as if each individual publication or patent application or reference were specifically and individually indicated to be incorporated by reference. Any material accompanying this application on compact disc or other recorded medium is incorporated by reference.

What is claimed is:

1. A method for increasing a CDK9/cyclin-dependent transcription in a cell, the method comprising the steps of: incubating in vitro a human cell comprising human 7SK RNA (SEQ ID NO: 1) and comprising an amount of active CDK9/cyclin, and in which a CDK9/cyclin-dependent transcription is to be increased; introducing in the cell a human 7SK RNA-binding antisense 7SK RNA which increases the amount of active CDK9/cyclin in the cell, and thereby increases said CDK9/cyclin-dependent transcription in the cell, wherein the antisense RNA consists of antisense of nucicotides 221–241 or 95–114 of human 7SK RNA (SEQ ID NO: 1); and detecting a resultant increase in CDK9/cyclin-dependent transcription in the cell, wherein the CDK9/cyclin-dependent transcription is selected from the group consisting of transcription from a recombinant construct, LTR promoter-controlled transcription and HIV transcription.

2. The method of claim 1, wherein the transcription is from a recombinant construct.

3. The method of claim 1, wherein the transcription is an LTR promoter-controlled transcription.

4. The method of claim 1, wherein the transcription is HIV transcription.

5. The method of claim 1, wherein the antisense RNA consists of antisense of nucleotides 221–241 of human 7SK RNA (SEQ ID NO:1).

6. The method of claim 2, wherein the antisense RNA consists of antisense of nucleotides 221–241 of human 7SK RNA (SEQ ID NO:1).

7. The method of claim 3, wherein the antisense RNA consists of antisense of nucleotides 221–241 of human 7SK RNA (SEQ ID NO:1).

8. The method of claim 4, wherein the antisense RNA consists of antisense of nucleotides 221–241 of human 7SK RNA (SEQ ID NO:1).

9. The method of claim 1, wherein the antisense RNA consists of antisense of nucleotides 95–114 of human 7SK RNA (SEQ ID NO:1).

10. The method of claim 2, wherein the antisense RNA consists of antisense of nucleotides 95–114 of human 7SK RNA (SEQ ID NO:1).

11. The method of claim 3, wherein the antisense RNA consists of antisense of nucleotides 95–114 of human 7SK RNA (SEQ ID NO:1).

12. The method of claim 4, wherein the antisense RNA consists of antisense of nucleotides 95–114 of human 7SK RNA (SEQ ID NO:1).

* * * * *

SEQUENCE LISTING

<160> NUMBER OF SEQ ID NOS: 9

<210> SEQ ID NO 1
<211> LENGTH: 330
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 1
ggatgtgagg gcgatctggc tgcgacatct gtcaccccat tgatcgccag ggttgattcg      60
gctgatctgg ctggctaggc gggtgtcccc ttcctccctc accgctccat gtgcgtccct     120
cccgaagctg cgcgctcggt cgaagaggac gaccatcccc gatagaggag gaccggtctt    180
cggtcaaggg tatacgagta gctgcgctcc cctgctagaa cctccaaaca agctctcaag    240
gtccatttgt aggagaacgt agggtagtca agcttccaag actccagaca catccaaatg    300
aggcgctgca tgtggcagtc tgcctttctt                                      330

<210> SEQ ID NO 2
<211> LENGTH: 191
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
ggatgtgagg gcgatctggc tgcgacatct gtcaccccat tgatcgccag ggttgattcg      60
gctgatctgg ctggctaggc gggtgtcccc ttcctccctc accgctccat gtgcgtccct     120
cccgaagctg cgcgctcggt cgaagaggac gaccatcccc gaggcgctgc atgtggcagt    180
ctgcctttct t                                                           191

<210> SEQ ID NO 3
<211> LENGTH: 191
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
ggaagtgagg gcgatctggc tgcgacatct gtcaccccat tgatcgccag ggttgattcg      60
gctgatctgg ctggctaggc gggtgtcccc ttcctccctc accgctccat gtgcgtccct     120
cccgaagctg cgcgctcggt cgaagaggac gaccatcccc gaggcgttgc atgtggcagt    180 cttcctttt t                                                            191

<210> SEQ ID NO 4
<211> LENGTH: 171
<212> TYPE: DNA
<213> ORGANISM: Artificial Sequence
<220> FEATURE:
<223> OTHER INFORMATION: Description of Artificial Sequence: Synthetic
      Sequence -continued

```
<400> SEQUENCE: 4
ggatgtgagg gcgatctggc tgcgacatct gtcaccccat tgatcgccag ggttgattcg      60
gctgatctgg ctggctaggc gggtgtcccc ttcctccctc accgctccat gtgcgtccct    120
cccgaagctg cgcgctcggt cgaagaggac gaccatcccc gaggcgttct t             171

<210> SEQ ID NO 5
<211> LENGTH: 161
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
gcgatctggc tgcgacatct gtcaccccat tgatcgccag ggttgattcg gctgatctgg     60
ctggctaggc gggtgtcccc ttcctccctc accgctccat gtgcgtccct cccgaagctg   120
cgcgctcggt cgaagaggac gaccatcccc gaggcgttct t                       161

<210> SEQ ID NO 6
<211> LENGTH: 181
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 6
ggatgtgagg gcgatctggc tgcgacatct gtcaccccat tgatcgccag ggttgattcg     60
gctgatctgg ctggctaggc gggtgtcccc ttcctccctc accgctccat gtgcgtccct   120
cccgaagctg cgcgctcggt cgaagaggac gaccatcccc gaggcgctgc atgcctttct   180
t                                                                    181

<210> SEQ ID NO 7
<211> LENGTH: 179
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 7
gagggcgatc tggctgcgac atctgtcacc ccattgatcg ccagggttga ttcggctgat     60
ctggctggct aggcgggtgt ccccttcctc cctcaccgct ccatgtgcgt ccctcccgaa   120
gctgcgcgct cggtcgaaga ggacgaccat ccccttgcat gtggcagtct ttttttttt    179

<210> SEQ ID NO 8
<211> LENGTH: 167
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8
gagggcgatc tggctgcgac atctgtcacc ccattgatcg ccagggttga ttcggctgat     60
ctggctggct aggcgggtgt ccccttcctc cctcaccgct ccatgtgcgt ccctcccgaa   120
gctgcgcgct cggtcgaaga ggacgaccat ccccgttttt tttttt                  167
```

```
<210> SEQ ID NO 9
<211> LENGTH: 148
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 9
gatctggctg cgacatctgt caccccattg atcgccaggg ttgattcggc tgatctggct        60
ggctaggcgg gtgtcccctt cctccctcac cgctccatgt gcgtgaagct gcgcgctcgg       120
tcgaagagga cgaccatccc cgtttttt                                          148
```